United States Patent
Baumann

(10) Patent No.: US 12,426,773 B2
(45) Date of Patent: *Sep. 30, 2025

(54) METHOD AND APPARATUS FOR CAPTURING IMAGES OF A MEDICAL SUBJECT WITH WHITE LIGHT AND FLUORESCENT LIGHT

(71) Applicant: KARL STORZ SE & Co KG, Tuttlingen (DE)

(72) Inventor: Christin Baumann, Tuttlingen (DE)

(73) Assignee: KARL STORZ SE & Co KG, Tuttlingen (DE)

( * ) Notice: Subject to any disclaimer, the term of this patent is extended or adjusted under 35 U.S.C. 154(b) by 964 days.

This patent is subject to a terminal disclaimer.

(21) Appl. No.: 17/548,082

(22) Filed: Dec. 10, 2021

(65) Prior Publication Data
US 2022/0183542 A1 Jun. 16, 2022

(30) Foreign Application Priority Data
Dec. 10, 2020 (DE) .......................... 102020132982.2

(51) Int. Cl.
*A61B 1/04* (2006.01)
*G01J 3/44* (2006.01)
(Continued)

(52) U.S. Cl.
CPC ............ *A61B 1/043* (2013.01); *G01J 3/4406* (2013.01); *G01N 21/6456* (2013.01);
(Continued)

(58) Field of Classification Search
CPC ........ A61B 1/043; H04N 23/56; H04N 23/45; G01J 3/4406; G01J 2003/2826;
(Continued)

(56) References Cited

U.S. PATENT DOCUMENTS 12,018,128 B2 * 6/2024 Sasaki ................ C08G 73/1085
12,108,128 B2 * 10/2024 Baumann ........... G01N 21/6456
(Continued)

FOREIGN PATENT DOCUMENTS

DE 202015011441 A1 3/2017
DE 102017203448 A1 9/2018
(Continued)

OTHER PUBLICATIONS

Mieog, J. S. D., S. L. Troyan, M. Hutteman, et al., "Toward Optimization of Imaging System and Lymphatic Tracer for Near-Infrared Fluorescent Sentinel Lymph Node Mapping in Breast Cancer," Annals of Surgical Oncology, 2011, pp. 2483-2491+supplemental, 18, Springer Nature, Swizerland.
(Continued)

*Primary Examiner* — James T Boylan
(74) *Attorney, Agent, or Firm* — David N. Villalpando; Jacqueline Cohen

(57) ABSTRACT

An image capture apparatus for capturing an image of an object of medical interest in reemitted and/or reflected illumination light, for capturing an image of the object in fluorescence light generated by protoporphyrin, and for capturing an image in fluorescence light generated by OTL38. The apparatus includes an image sensor for capturing blue, green and red light, another image sensor for capturing fluorescence light from protoporphyrin and OTL38, and a beam splitter for guiding light from the object that has a wavelength shorter than a predetermined threshold wavelength $\lambda_0$ to the first image sensor, and for guiding light from the object that has a wavelength longer than the predetermined threshold wavelength $\lambda_0$ to the second image sensor. A filter arranged upstream of the second image sensor partially, extensively or completely suppresses light
(Continued)

at a wavelength suitable for exciting fluorescence of OTL38. A corresponding method is also presented.

3 Claims, 5 Drawing Sheets

(51) Int. Cl.
  *G01N 21/64* (2006.01)
  *H04N 23/45* (2023.01)
  *H04N 23/56* (2023.01)
  *G01J 3/28* (2006.01)
  *G01N 33/574* (2006.01)

(52) U.S. Cl.
  CPC .......... *G01N 21/6486* (2013.01); *H04N 23/45* (2023.01); *H04N 23/56* (2023.01); *G01J 2003/2826* (2013.01); *G01N 2021/6439* (2013.01); *G01N 33/57492* (2013.01)

(58) Field of Classification Search
  CPC .......... G01N 21/6456; G01N 21/6486; G01N 33/57492; G01N 2021/6439
  See application file for complete search history.

(56) References Cited

U.S. PATENT DOCUMENTS

| | | | |
|---|---|---|---|
| 2007/0260132 A1* | 11/2007 | Sterling | A61B 5/14551 600/323 |
| 2017/0167980 A1 | 6/2017 | Dimitriadis et al. | |
| 2017/0176336 A1 | 6/2017 | Dimitriadis et al. | |
| 2017/0209050 A1* | 7/2017 | Fengler | H04N 23/16 |
| 2018/0364470 A1* | 12/2018 | Hauger | G02B 21/0012 |
| 2019/0170647 A1 | 6/2019 | Ikenaga et al. | |
| 2021/0137369 A1* | 5/2021 | Meester | A61B 1/0646 |
| 2021/0267443 A1* | 9/2021 | Baumann | H04N 25/61 |
| 2022/0151495 A1* | 5/2022 | Walle-Jensen | A61B 5/0077 |
| 2022/0191365 A1* | 6/2022 | Baumann | H04N 23/55 |

FOREIGN PATENT DOCUMENTS

| | | | |
|---|---|---|---|
| WO | 2015185661 A1 | 12/2015 | |
| WO | WO-2017036600 A1 * | 3/2017 | ........... G01J 3/2803 |
| WO | 2020052626 A1 | 3/2020 | |

OTHER PUBLICATIONS

Troyan, S. L., V. Kianzad, S. L. Gibbs-Strauss, et al., "The FLARE Intraoperative Near-Infrared Fluorescence Imaging System: A First-in-Human Clinical Trial in Breast Cancer Sentinel Lymph Node Mapping," Annals of Surgical Oncology, 2009 pp. 2943-2952, 16, Springer Nature, Swizerland.

Baust, "Prüfungsbescheid (German Report on Patentability)," Nov. 30, 2021, pp. 1-7, German Patent Office, Munich.

Predina, J.D., A.D. Newton, et al., "An open label trail of folate receptor-targeted intraoperative molecular imaging to localize pulmonary squamous cell carcinomas," Oncotarget, 2018, pp. 13517-13529, vol. 9, No. 17, Impact Journals, Orchard Park, USA.

Food and Drug Administration, "FDA approves pafolacianine for identifying malignant ovarian cancer lesions," Press Release, Dec. 1, 2021, pp. 1-2, Food and Drug Administration, USA.

Tanyi, Janos L., et al., "A Phase III Study of Pafolacianine Injection (OTL38) for Intraoperative Imaging of Folate Receptor-Positve Ovarian Cancer (Study 006)," (Astract), J. Clinical Oncology, 2023, pp. 276-284, V. 41, No. 2, American Society of Clinical Oncology, USA.

* cited by examiner

METHOD AND APPARATUS FOR CAPTURING IMAGES OF A MEDICAL SUBJECT WITH WHITE LIGHT AND FLUORESCENT LIGHT

CROSS REFERENCE TO RELATED APPLICATIONS

This application claims priority to German Patent Application No. 102020132982.2, filed Dec. 10, 2020, and entitled, "Erfassung von Bildern eines medizinischen Objekts in WeiBlicht and Fluoreszenzlicht," and is incorporated herein by reference.

TECHNICAL FIELD OF THE INVENTION

The present invention relates to an apparatus, a system and a method for capturing images of an object of medical interest in reflected or reemited light and in fluorescence light.

BACKGROUND OF THE INVENTION

In some imaging diagnostic methods, an image of an object of medical interest (sometimes referred to herein as a medical object) illuminated by white light and an image of the medical object in fluorescence light are captured simultaneously or in succession.

For photodynamic diagnosis (PDD), δ-aminolevulinic acid (abbreviated dALA, δ-ALA or SALA) is administered topically. Protoporphyrin IX (PpIX) which accumulates more in tumors than in healthy tissue arises within the scope of haem biosynthesis. Protoporphyrin IX can be excited by light in the wavelength range of 380 nm to 450 nm (violet to blue; absorption maximum at 405 nm) and subsequently emits fluorescence light in the wavelength range from 600 nm to 750 nm (red; emission maximum at 630 nm to 640 nm).

OTL38 is a further fluorophore, the use of which is described for example in the article "An open label trial of folate receptor-targeted intraoperative molecular imaging to localize pulmonary squamous cell carcinomas" by Jarrod D. Predinae from 2018 (Oncotarget Vol. 9 (No. 17) 13517-13529) and which has an absorption maximum at 774 nm to 776 nm and a fluorescence maximum at 794 nm to 796 nm.

Two cameras can be used to capture reemitted (diffusely reflected/scattered) white light and to capture fluorescence light. A first camera captures the image in the visible spectral range resulting from the illumination of the medical object with white light, while a second camera captures the fluorescence light. Both cameras can be coupled to a single endoscope or a single lens, for example by way of a dichroically reflecting surfaces, in order to capture both images from the same perspective.

WO 2015/185661 A1 describes the alternating illumination of an object with light from different spectra and the synchronously alternating capture of images of the object using a common image sensor (page 6, last paragraph to page 7, fifth paragraph; FIGS. 1 and 2). In a phase 1, the object is illuminated by light having a spectrum with a plurality of regions of high intensity and a region of low intensity, the latter comprising longer wavelengths than a region of high intensity. In a phase 2, the object is illuminated by light having a broad spectrum. In both phases, light emitted or reemitted by the object is captured by the same image sensor. In phase 1, the spectral bands of the light reflected by the object are attenuated and substantially only the fluorescence emission is transmitted and captured by the image sensor. In phase 2, light reflected by the object is transmitted and captured by the image sensor.

WO 2017/036600 A1 describes a fluorescence light detection system and a microscopy system (title; abstract; page 1, first paragraph; page 3, first complete paragraph). The fluorescence light detection system 19D comprises a beam splitter system 35D which directs light with wavelengths longer than a threshold wavelength $\lambda_0$ to a first camera 21D and light with wavelengths shorter than the threshold wavelength $\lambda_0$ to a second camera 23D (page 36, only complete paragraph; FIG. 6). The threshold wavelength $\lambda_{90}$ can be located in the range from 600 nm to 630 nm, wherein fluorescence light of protoporphyrin IX is substantially only transmitted to the first camera 21 (ibid).

US 2019/0170647 A1 describes an imaging system (title, abstract, paragraphs [0001] and [0008]). A camera head 105c comprises a color splitting prism 201c, a first image recording element for recording an image 1051a in visible light, a second image recording element for recording an image 1051b in visible light and a third image recording element for recording an image 1052 in near infrared light (paragraphs [0139] and [0150]; FIG. 10). A dichroic film 223 of the color splitting prism 201c reflects near infrared light to the third image recording element and transmits visible light. A dichroic film 225 of the color splitting prism 201c reflects red visible light to the first image recording element and transmits blue and green visible light to the second image recording element (ibid).

An object of the present invention consists of developing an improved image capture apparatus, an improved image capture system and an improved method for capturing an image of a medical object in reemitted and/or reflected illumination light and for capturing an image of the medical object in fluorescence light generated by protoporphyrin and for capturing an image of the medical object in fluorescence light generated by OTL38.

SUMMARY OF THE INVENTION

An image capture apparatus for capturing an image of an object of medical interest (also referred to herein as a medical object) in reemitted and/or reflected illumination light and for capturing an image of the medical object in fluorescence light generated by protoporphyrin and for capturing an image of the medical object in fluorescence light generated by OTL38 comprises a first image sensor for capturing blue, green and red light, a second image sensor for capturing fluorescence light from protoporphyrin and OTL38, a beam splitter for guiding light which emanates from the object and has a wavelength shorter than a predetermined threshold wavelength $\lambda_0$ within the red spectral range to the first image sensor and for guiding light which emanates from the object and has a wavelength longer than the predetermined threshold wavelength $\lambda_0$ to the second image sensor, and a filter arranged upstream of the second image sensor in the light path, for partial, extensive or complete suppression of light at a wavelength suitable for exciting fluorescence of OTL38.

The image capture apparatus is provided and designed to capture images of a medical object within a natural or artificial cavity or on an outer surface of the body of a human or animal patient. To this end, the image capture apparatus comprises interfaces, in particular mechanical, optical and electrical interfaces, to other apparatuses which are approved for use in operating theatres, treatment rooms and other medical establishments.

Further, the image capture apparatus can be sterilizable, in particular autoclavable. To this end, the image capture apparatus has in particular a fluid-tight or hermetically tight closed outer surface and can be exposed without being damaged to sterilizing media, for example steam at excess pressure and 140° C., over a relatively long period of time.

The image capture apparatus can have a monocular embodiment, i.e. only provide one image signal representing a single image at all times and in each spectral range or for each color channel. Alternatively, the image capture apparatus can be designed to capture stereo images, i.e. capture two images simultaneously in one and the same spectral range or for the same color channel and generate two image signals which represent these two captured images. This can apply to all spectral regions or color channels, or only to individual spectral regions or color channels.

The image capture apparatus can comprise a camera which can be coupled to a standard eyepiece of an endoscope, or of an exoscope or of a surgical microscope. Alternatively, the image capture apparatus itself can be designed as an endoscope, in particular a video endoscope, as an exoscope or as a surgical microscope.

In particular, the image capture apparatus is provided and designed to capture fluorescence of protoporphyrin IX (in the spectral range of 600 nm to 700 nm, with a maximum at 630 nm to 640 nm) and to capture fluorescence of OTL38 (with a maximum at approximately 793 nm to 796 nm).

The first image sensor is provided and designed to capture light in the wavelength ranges perceived as blue, green and red by the healthy human eye. To this end, the first image sensor captures in particular both light in a wavelength range below 490 nm and light in a wavelength range between 490 nm and 585 nm, and light in a wavelength range above 585 nm. In this case, the first image sensor does not capture the entire wavelength range from 585 nm to 750 nm, which is perceived as orange or red by the healthy human eye, and also does not capture the entire wavelength range down to 380 nm, which is perceived as violet or blue by the healthy human eye, or does not capture this range with constant sensitivity throughout.

By way of example, the beam splitter comprises a dichroic layer in an otherwise optically transparent prism. Since a filter edge does not correspond to a step function, the wavelength at which half of the radiated-in light at this wavelength is guided to the first image sensor and the other half is guided to the second image sensor is referred to as threshold wavelength $\lambda_0$ in the present case.

The filter suppresses light with a wavelength suitable for exciting fluorescence of OTL38. To this end, the characteristic of the filter, i.e., the wavelength dependence of its transmission, is matched in particular to the characteristic of the light source used to excite fluorescence of OTL38, i.e., to the emission spectrum of the light source. The more narrowband the emission spectrum of the light source, the narrower the wavelength range suppressed by the filter may be. Light at a certain wavelength is suppressed by the filter if the intensity or the luminous flux of the light following the passage through the filter is less than before. A complete suppression, i.e., the complete removal of all photons of a given wavelength, represents an ideal case not always readily attainable in practice.

The filter can be arranged directly upstream of the second image sensor in the light path, i.e., immediately in front of the second image sensor in the propagation direction of the light to be captured and can therefore be arranged between the beam splitter and the image sensor. By way of example, the filter can be arranged at a light-exit surface of the beam splitter or at a light-entry surface of the image sensor, i.e., immediately in front of the light-sensitive layer of the image sensor. Alternatively, the filter can be arranged upstream of the beam splitter in the propagation direction of the light to be captured, for example between an objective and the beam splitter or even upstream of an objective in the light path.

The image capture apparatus comprises a first image sensor, which can be largely or completely similar to, or the same as, a conventional image sensor for capturing an image in reemitted and/or reflected white light. Apart from limitations, albeit partly correctable limitations, on account of parts of the spectral range perceived as orange to red by the healthy human eye missing, and optionally on account of parts of the blue spectral range missing, the first image sensor therefore captures a conventional color image in reemitted or reflected white light.

Both fluorescence light emanating from protoporphyrin and fluorescence light emanating from OTL38 are only captured by the second image sensor. Fluorescence of protoporphyrin and OTL38 can be excited simultaneously or sequentially and can be captured by the second image sensor.

If the second image sensor is a monochrome image sensor, i.e., only has one color channel, it is not possible to distinguish between fluorescence light of protoporphyrin and fluorescence light of OTL38 in the case of the simultaneous excitation and capture. In this case, images in fluorescence light of protoporphyrin and images in fluorescence light of OTL38 can be generated alternately in the case of an alternating excitation of the fluorescence of protoporphyrin and the fluorescence of OTL38.

If the second image sensor has separate color channels for the capture of fluorescence light of protoporphyrin and for the capture of fluorescence light of OTL38, it is possible to simultaneously capture an image in fluorescence light of protoporphyrin and an image in fluorescence light of OTL38.

In this way it is possible to simultaneously capture a white-light image with a fluorescence image of protoporphyrin and simultaneously capture a white-light image with a fluorescence image of OTL38. The representation on a monitor can also be implemented simultaneously and in superimposed fashion in each case, facilitating improved orientation and recognition of the fluorescing tissue for the user. As explained above, the simultaneous representation of a white-light image, a protoporphyrin fluorescence image and OTL38 fluorescence image can also be attained using suitable image sensors.

In the case of sequential capture and illumination, an image captured by means of the second image sensor during a time interval without excitation of fluorescence can be used to correct or complement the red color channel of the first image sensor, and hence the white-light image. Expressed differently, there can be alternating illumination with white light and with protoporphyrin excitation light. During the white light illumination, a white-light image is captured on both sensors and the different wavelength ranges of the sensors are used to generate a normal white-light image having the optical wavelengths. Only the second image sensor is read during the excitation illumination in order to capture the protoporphyrin fluorescence light.

To improve the recognizability of the fluorescence in the case of simultaneous illumination and image capture, the white light illumination can be reduced or greatly reduced or completely blocked at wavelengths in the range of the protoporphyrin emission, for example in the case of wavelengths longer than 625 nm, by way, for example, of an illumination filter or corresponding control of the white light source. In particular, only the range of the emission of protoporphyrin fluorescence is filtered in this way at the white light source in order to make the fluorescence better recognizable in this range and prevent it from being swamped.

For an optimized recognition of the OTL38 fluorescence in the case of simultaneous illumination and capture of white light and OTL38 fluorescence, the white light source might only provide light at wavelengths of shorter than approximately 700 nm for illumination purposes.

In the case of an image capture device as described here, the threshold wavelength $\lambda_0$ is shorter than the wavelength of the fluorescence maximum of protoporphyrin, in particular.

In the case of an image capture apparatus as described here, the threshold wavelength $\lambda_0$ is not longer than 640 nm, in particular.

In the case of an image capture apparatus as described here, the threshold wavelength $\lambda_0$ is not shorter than 610 nm or 620 nm and not longer than 630 nm or 640 nm, in particular.

The steeper the filter edge of the beam splitter, the longer the threshold wavelength $\lambda_0$ can be, and hence the more completely the orange and red spectral range can be captured by the first image sensor. The shorter the threshold wavelength $\lambda_0$, the greater the proportion of the fluorescence light of protoporphyrin captured by the second image sensor, and the smaller the falsification of the white-light image captured by the first image sensor as a result of fluorescence light of protoporphyrin.

In the case of an image capture apparatus as described here, the filter suppresses light with a wavelength in the range from 720 nm or 730 nm or 740 nm or 750 nm to 770 nm or 780 nm or 790 nm, in particular.

In the case of an image capture apparatus as described here, the filter suppresses light at wavelengths within an interval whose lower boundary is no shorter than 700 nm or no shorter than 730 nm or no shorter than 740 nm or no shorter than 750 nm or no shorter than 760 nm and whose upper boundary is no longer than 780 nm or no longer than 790 nm or no longer than 800 nm or no longer than 820 nm or no longer than 850 nm, in particular.

Within the wavelength interval, the intensity of the light that has passed through the filter is for example less than one half, in particular less than one third or less than one fifth or less than one tenth of the intensity upstream of the filter. Outside of the wavelength interval, the intensity of the light that has passed through the filter is for example more than one half, in particular more than two thirds or more than four fifths or more than nine tenths of the intensity upstream of the filter. The filter edges, i.e., the rising or falling sections of the transmission curve at the boundaries of the interval, are not, in reality, step functions, and the bounds or the terms "within" and "outside of" should therefore not be understood to include nanometer accuracy. The boundary could be defined as the centre of the rising or falling transmission curve at the ends of the interval, or else as the points of minimum or maximum transmission in the area of the interval ends. This is known to a person skilled in the art.

The more narrowband the light exciting the fluorescence of OTL38 is radiated in, the more narrowband the filter design can be in order to suppress the capture of reemitted and/or reflected excitation light by the second image sensor.

An image capture apparatus as described here further comprises, in particular, an objective, at least either for generating an image of the medical object in illumination light reemitted and/or reflected by the object or for generating an image of the medical object in fluorescence light emanating from the object.

In the case of an image capture apparatus as described here, the objective is provided and designed in particular for generating an image of the medical object in illumination light reemitted and/or reflected by the object and for generating an image of the medical object in fluorescence light emanating from the object, with the beam splitter being arranged between the objective and the image sensors.

In this case, the objective is provided and designed in particular both for imaging in the wavelength range below the threshold wavelength $\lambda_0$ and for imaging in the wavelength range above the threshold wavelength $\lambda_0$. The beam splitter is arranged downstream of the objective in the light path and upstream of the image sensors in the light path.

An image capture apparatus as described here further comprises, in particular, a further filter which is arranged upstream of the first image sensor in the light path for the partial, extensive or complete suppression of light with a wavelength suitable for the excitation of fluorescence of protoporphyrin.

The suppression of excitation light, i.e., the reduction of the intensity thereof, can prevent swamping of the image captured by the first image sensor, in particular of the blue color channel thereof, by reemitted or reflected excitation light and can facilitate a natural color impression when the excitation light has a higher intensity than the remaining light provided for illuminating the medical object. A partial or extensive but incomplete suppression of the reemitted or reflected excitation light can facilitate a particularly natural color reproduction.

In the case of an image capture apparatus as described here, the further filter suppresses, in particular, light with a wavelength ranging from 380 nm to 450 nm.

In the case of an image capture apparatus as described here, the further filter suppresses, in particular, light with a wavelength ranging from 400 nm to 430 nm.

In the case of an image capture apparatus as described here, the further filter suppresses, in particular, light with wavelengths below a further threshold wavelength $\lambda_1$ and passes light with wavelengths above the further threshold wavelength $\lambda_1$, the further threshold wavelength $\lambda_1$ being no longer than 410 nm or no longer than 420 nm or no longer than 430 nm or no longer than 440 nm.

In the case of an image capture apparatus as described here, the further filter is arranged, in particular, between the beam splitter and the first image sensor.

By way of example, the further filter is arranged at a light-exit surface of the beam splitter or at a light-entry surface of the first image sensor. Alternatively, the further filter can be arranged upstream of the beam splitter, for example between an objective and the beam splitter or upstream of an objective in the light path.

An image capture apparatus as described here is provided and designed, in particular, to capture a stereo image.

To this end, the image capture apparatus comprises for example two first image sensors and two second image sensors, wherein in each case a first image sensor and a second image sensor are provided and designed to capture an image provided for the reproduction for the left eye and a first image sensor and a second image sensor are provided and designed to capture an image provided for the reproduction for the right eye. Alternatively, the first image sensor and/or the second image sensor can each be so large that an image provided for the reproduction for the left eye and an image provided for the reproduction with the right eye can be captured thereon, next to one another in each case.

An image capture system for capturing an image of a medical object in reemitted and/or reflected illumination light and for capturing an image of the medical object in fluorescence light generated by protoporphyrin and for capturing an image of the medical object in fluorescence light generated by OTL38 comprises a light-source device for alternately or simultaneously generating illumination light in the blue, green and red wavelength range, first excitation light for exciting fluorescence of protoporphyrin and second excitation light for exciting the fluorescence of OTL38, and an image capture apparatus as described herein.

The light-source device is provided and designed, in particular, for alternate or simultaneous generation of illumination light within the wavelength range from 410 nm or 420 nm or 430 nm or 440 nm to 610 nm or 620 nm or 630 nm or 640 nm and first excitation light in the wavelength range from 370 nm to 420 nm and second excitation light in the wavelength range from 740 nm or 750 nm to 770 nm or 780 nm. For the generation of the illumination light, for the generation of the first excitation light and for the generation of the second excitation light, the light-source device in each case has a separately controllable light source, in particular.

In the case of an image capture system as described herein, the further filter transmits, in particular, some of the reemitted and/or reflected first excitation light in order to facilitate a natural color impression.

In the case of an image capture system as described herein, the light-source device comprises, in particular, a light-emitting diode or a laser for generating excitation light with a wavelength ranging from 370 nm to 420 nm and a light-emitting diode or a laser for generating excitation light with a wavelength ranging from 740 nm or 750 nm to 770 nm or 780 nm.

A method for capturing an image of a medical object in reemitted and/or reflected illumination light and for capturing an image of the medical object in fluorescence light generated by protoporphyrin and for capturing an image of the medical object in fluorescence light generated by OTL38 comprises irradiating the medical object with illumination light in the blue, green and red spectral range, irradiating the medical object with first excitation light for exciting fluorescence of protoporphyrin, irradiating the medical object with second excitation light for exciting fluorescence of OTL38, capturing a color image of the medical object in the blue, green and red spectral range by means of a first image sensor and capturing a fluorescence image of the medical object in the red and infrared spectral range by means of a second image sensor, wherein reemitted and/or reflected second excitation light is not captured or only partly captured by the second image sensor.

In particular, the method is carried out using an image capture apparatus as described herein or using an image capture system as described herein.

In the case of a method as described here, a filter upstream of the second image sensor in the light path suppresses, in particular, reemitted and/or reflected second excitation light in a partial, extensive or complete manner.

In the case of a method as described herein, irradiating with illumination light in the blue, green and red spectral range, irradiating with the first excitation light, irradiating with the second excitation light, capturing the color image in the blue, green and red spectral range by means of the first image sensor and capturing the fluorescence image in the red and infrared spectral range by means of the second image sensor at least intermittently occur at the same time, in particular.

Irradiating with illumination light in the blue, green and red spectral range, irradiating with the first excitation light, irradiating with the second excitation light, capturing the color image in the blue, green and red spectral range by means of the first image sensor and capturing the fluorescence image in the red and infrared spectral range by means of the second image sensor can occur completely at the same time. Alternatively, it is for example only irradiating with illumination light in the blue, green and red spectral range and capturing the color image in the blue, green and red spectral range by means of the first image sensor and capturing an image in the red and infrared spectral range by means of the second image sensor that occur at the same time, wherein the image captured by means of the second image sensor can be used to correct a red color channel of the color image captured by means of the first image sensor. Alternatively, irradiating with illumination light in the blue, green and red spectral range, irradiating with the first excitation light, capturing the color image in the blue, green and red spectral range by means of the first image sensor and capturing the fluorescence image in the red and infrared spectral range by means of the second image sensor occur at the same time, but not irradiating with the second excitation light, in order to simultaneously capture a color image and a fluorescence image only in fluorescence light of protoporphyrin. Alternatively, irradiating with illumination light in the blue, green and red spectral range, irradiating with the second excitation light, capturing the color image in the blue, green and red spectral range by means of the first image sensor and capturing the fluorescence image in the red and infrared spectral range by means of the second image sensor occur at the same time, but not irradiating with the first excitation light, in order to simultaneously capture a color image by means of the first image sensor and a fluorescence image only in fluorescence light of OTL38 by means of the second image sensor.

A method as described herein further comprises, in particular, irradiating the medical object with illumination light in the blue, green and red spectral range or irradiating the medical object with red light in the red spectral range, capturing a red light image of the medical object in the red spectral range by means of the second image sensor while irradiating the medical object with illumination light in the blue, green and red spectral range or with red light in the red spectral range, and correcting the red color channel of the color image on the basis of the red light image.

In the case of a method as described herein, the medical object is not, in particular, irradiated by the second excitation light while the red light image is captured.

In the case of a method as described herein, the medical object is not, in particular, irradiated by the first excitation light while the red light image is captured.

BRIEF DESCRIPTION OF THE DRAWINGS

Embodiments are explained in more detail below on the basis of the attached figures, in which.

DETAILED DESCRIPTION OF THE REPRESENTATIVE EMBODIMENTS

Figure 1:
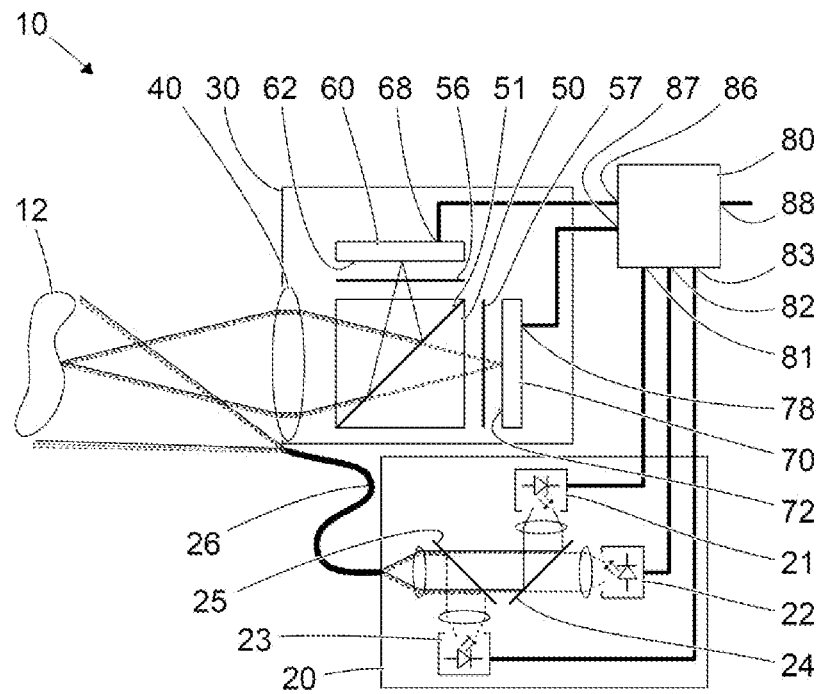
FIG. 1 shows a schematic illustration of an image capture system.

FIG. 1 shows a schematic illustration of an image capture system 10 for capturing an image of a medical object 12 in reemitted and/or reflected illumination light, for capturing an image of the medical object in fluorescence light emanating from protoporphyrin and for capturing an image in fluorescence light emanating from OTL38. The medical object 12 can be arranged within a cavity or on a surface of a body of a human or animal patient. Accordingly, the image capture system 10 can be arranged completely or partly within or completely outside of the body of a human or animal patient.

By way of example, the image capture system 10 can be an endoscope, an exoscope or a surgical microscope, or comprise an endoscope, an exoscope or a surgical microscope.

The observation of fluorescence light, in particular the observation of images in fluorescence light can facilitate or simplify a diagnosis. Protoporphyrin has a higher concentration in tumors than in healthy tissue, and so a distinction between healthy tissue and neoplasias can be made on the basis of the fluorescence of protoporphyrin. OTL38 has a higher concentration in tumors than in healthy tissue, and so tumor tissue can be distinguished particularly well from healthy tissue in the fluorescence light of OTL38.

The image capture system 10 comprises a light-source device 20 having a first light source 21, a second light source 22, a third light source 23, a first dichroically reflecting surface 24 and a second dichroically reflecting surface 25. FIG. 1 indicates that each of the light sources 21, 22, 23 comprises a light-emitting diode for generating light. Additionally or alternatively, each light source 21, 22, 23 can comprise one or more semiconductor lasers or other lasers, further light-emitting diodes or other light sources.

The first light source 21 is designed to generate broadband illumination light, the spectrum of which has components in the wavelength range perceived as blue by the healthy human eye, in the wavelength range perceived as green by the healthy human eye and in the wavelength range perceived as orange to red by the healthy human eye. To this end, the first light source 21 for example comprises one or more light-emitting diodes originally emitting in the wavelength range perceived as blue or violet by the healthy human eye, and a luminescence layer which absorbs some of the blue or violet light and emits light in the wavelength ranges perceived as red and green by the healthy human eye. Alternatively, the first light source 21 for example comprises a plurality of light-emitting diodes that each emit approximately in monochromatic fashion, i.e., with a narrow bandwidth at various wavelengths, and these together cover a range of wavelengths that is as large as possible between a lower boundary at approximately 400 nm to 430 nm and an upper boundary at approximately 700 nm to 750 nm.

The second light source 22 is provided and designed to emit narrowband first excitation light for exciting the fluorescence of protoporphyrin IX. To this end, the second light source 22 emits light that is as narrowband as possible and as intensive as possible, within the wavelength range of approximately 380 nm to approximately 450 nm, for example at approximately 405 nm, the absorption maximum of protoporphyrin IX.

The third light source 23 is provided and designed to emit narrowband second excitation light for exciting the fluorescence of OTL38. To this end, the third light source 23 emits light that is in particular as narrowband as possible and as intensive as possible, within the wavelength range between 700 nm and 850 nm, for example at approximately 770 nm to 780 nm, the absorption maximum of OTL38.

The first dichroically reflecting surface 24 completely reflects illumination light emitted by the first light source 21, or reflects this light to the greatest possible extent, and completely transmits first excitation light emitted by the second light source 22, or transmits this light to the greatest possible extent, such that the illumination light generated by the first light source 21 and the first excitation light generated by the second light source 22 are superposed as completely as possible. The second dichroically reflecting surface 25 completely reflects second excitation light emitted by the third light source 23, or reflects this light to the greatest possible extent, and completely transmits illumination light generated by the first light source 21 and first excitation light generated by the second light source 22, or transmits this light to the greatest possible extent, such that the illumination light generated by the first light source 21, the first excitation light generated by the second light source 22 and the second excitation light generated by the third light source 23 are superposed as completely as possible. The light from the light sources 21, 22, 23 which has been superposed as completely as possible, i.e., combined, is coupled into an optical waveguide 26 and guided to the medical object 12.

The dichroically reflecting surfaces 24, 25 of the light-source device 20 represent examples of devices for superposing or combining the light generated by the light sources 21, 22, 23. Alternatively, use can be made of polarization-dependently reflecting surfaces or other devices—especially if the light sources 21, 22, 23 generate polarized light.

The image capture system 10 further comprises an image capture apparatus 30. The image capture apparatus 30 can be a camera or part of a camera. Alternatively, the image capture apparatus 30 can be an endoscope or an exoscope or a surgical microscope, or can be part of an endoscope or of an exoscope or of a surgical microscope. The image capture apparatus 30 comprises an objective 40 for imaging the medical object 12, i.e., for generating a real image of the medical object 12, and a beam splitter 50 with a dichroically reflecting surface 51 in an otherwise optically transparent prism. A first filter 56 in front of a first image sensor 60 and a second filter 57 in front of a second image sensor 70 are arranged downstream of the beam splitter 50 in the light path. The objective 40 generates real images of the medical object 12 in light-sensitive layers 62, 72 of the image sensors 60, 70. By way of example, the light-sensitive layers 62, 72 of the image sensors 60, 70 are represented by surfaces of the image sensors 60, 70 that face the beam splitter 50.

The dichroically reflecting surface 51 of the beam splitter 50 causes an image of the medical object 12 in reemitted and/or reflected illumination light of the first light source 21 to arise in the light-sensitive layer 62 of the first image sensor 60, said image being referred to as a color image below, and causes an image of the medical object 12 in fluorescence light emitted by the medical object 12 to arise in the light-sensitive layer 72 of the second image sensor 70, said image being referred to as fluorescence image below. To this end, the dichroically reflecting surface 51 of the beam splitter 50 substantially completely and essentially exclusively reflects light with wavelengths that are shorter than a threshold wavelength $\lambda_0$, and substantially completely and essentially exclusively transmits light with wavelengths that are longer than the threshold wavelength $\lambda_0$. The threshold wavelength $\lambda_0$ ranges between 600 nm and 640 nm, in particular is located at 620 nm or 630 nm. As a result, some of the light reemitted and/or reflected by the medical object 12 within the light perceived as orange or red by the healthy human eye is incident on the first image sensor 60 and is captured in the latter's red color channel Therefore, a substantially normal or natural color impression can be generated using only the color image captured by the first image sensor 60.

Both fluorescence light generated by protoporphyrin IX in the medical object 12 and fluorescence light generated by OTL38 in the medical object 12 are captured by the second image sensor 70. The second image sensor 70 can be a monochromatic image sensor, i.e., have only one color channel. Alternatively, the second image sensor 70 can have a plurality of color channels, one of which exclusively or substantially exclusively captures the fluorescence of protoporphyrin IX and another one of which exclusively or substantially exclusively captures the fluorescence of OTL38.

The first filter 56 between the beam splitter 50 and the first image sensor 60 suppresses first excitation light, which is generated by the second light source 22 and reemitted and/or reflected by the medical object 12 without a wavelength change, in order to avoid a blue tint of the color image captured by the first image sensor 60. To this end, the first filter 56 particularly suppresses light with a wavelength shorter than a further threshold wavelength $\lambda_1$. The further threshold wavelength $\lambda_1$ ranges between 410 nm and 440 nm in particular, preferably at approximately 430 nm.

To also capture the reemission and reflection properties of the medical object 12 at wavelengths shorter than the further threshold wavelength $\lambda_1$, the first filter 56 can be formed in front of the first image sensor 60 such that some of the first excitation light, which is generated by the second light source 22 and reemitted by the medical object 12, can reach the first image sensor 60 and can contribute to generating the color image in the light-sensitive layer 62 of the first image sensor 60.

The second filter 57 in front of the second image sensor 70 is provided and designed to suppress second excitation light, which is generated by the third light source 23 and reemitted by the medical object 12. To this end, the second filter 57 suppresses, in particular, light in a wavelength range with a lower limit at 700 nm to 750 nm and an upper limit at 780 nm to 790 nm, said wavelength range being as narrow as possible and including, as completely as possible, the spectrum of the second excitation light generated by the third light source 23.

The second filter 57 can be designed to suppress the light, which is generated by the third light source 23 and reemitted and/or reflected by the medical object 12, only extensively but not completely. Hence, the reemission and reflection properties of the medical object 12 at the wavelengths suppressed by the second filter 57 can also contribute to generate the color image in the light-sensitive layer 72 of the second image sensor 70.

At an image signal output 68, the first image sensor 60 provides a first image signal which represents the color image captured by the first image sensor 60. At an image signal output 78, the second image sensor 70 provides a second image signal which represents the fluorescence image captured by the second image sensor 70.

The image capture system 10 further comprises a camera control unit (CCU) 80 with a first control output 81, which is coupled to the first light source 21, a second control output 82, which is coupled to the second light source 22, a third control output 83, which is coupled to the third light source 23, a first image signal input 86, which is coupled to the image signal output 68 of the first image sensor 60, a second image signal input 87, which is coupled to the image signal output 78 of the second image sensor 70, and an image signal output 88. The camera control unit 80 controls the light sources 21, 22, 23 of the light-source device 20 and the image sensors 60, 70, receives and processes the image signals provided by the image sensors 60, 70 and provides at an image signal output 88 an image signal containing information from both image signals provided by the image sensors 60, 70.

In particular, the image signal provided at the image signal output 88 by the camera control unit 80 represents a color image of the medical object in which tumor tissue recognizable on the basis of the fluorescence of protoporphyrin IX and/or tumor tissue recognizable on the basis of the fluorescence of OTL38 are emphasized. The emphasis can be implemented in each case by way of color, intensity, or time-dependent modulation, for example.

Figure 4:
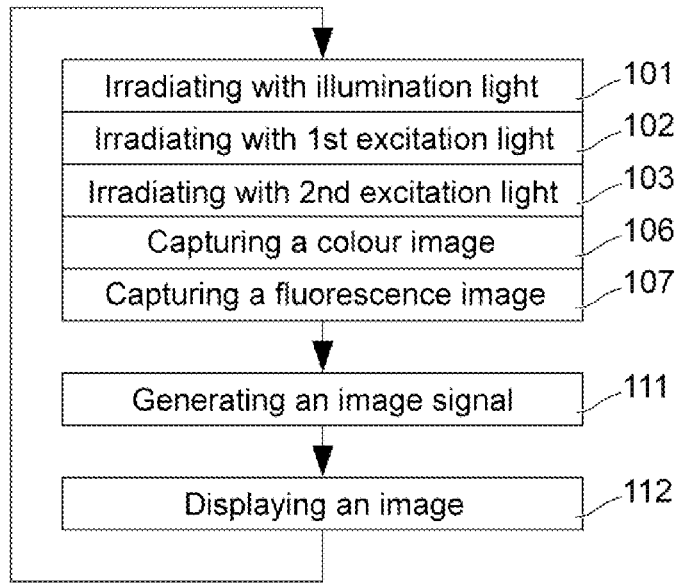
FIG. 4 shows a schematic flowchart of a method for capturing images.
Figure 5:
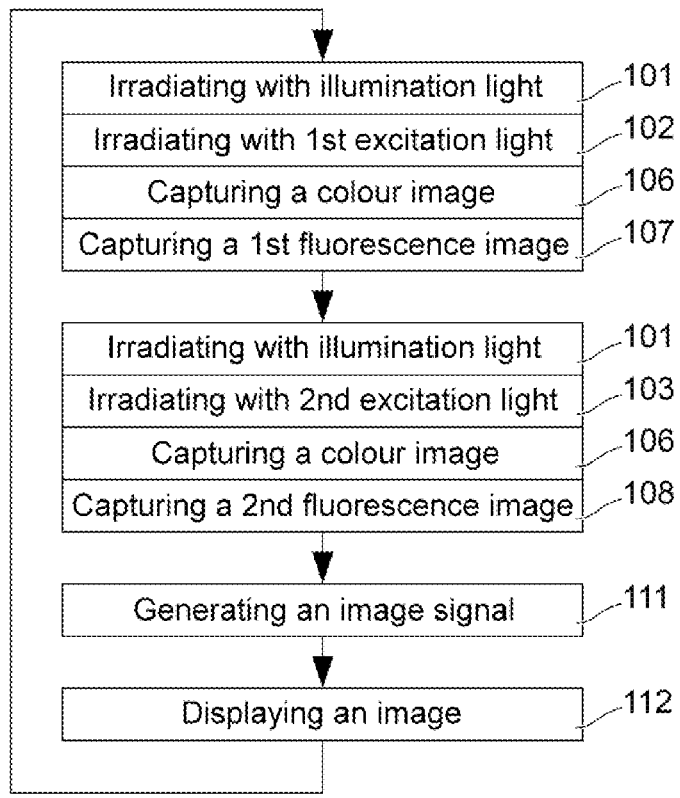
FIG. 5 shows a schematic flowchart of a further method for capturing images.
Figure 6:
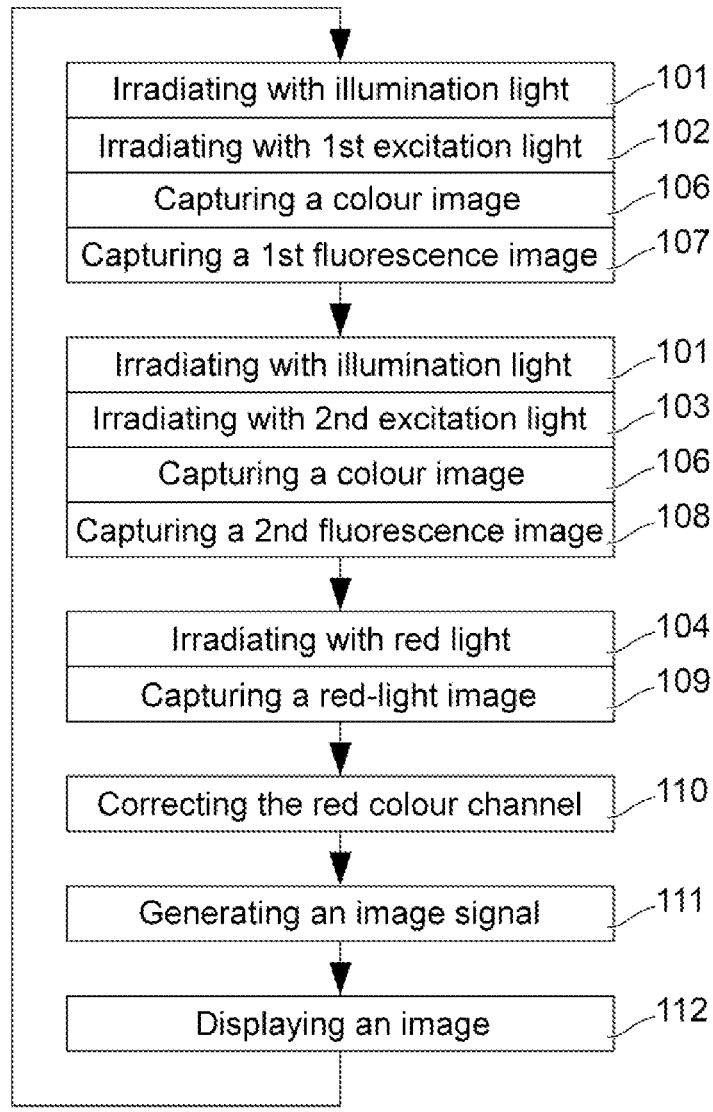
FIG. 6 shows a schematic flowchart of a further method for capturing images.

In particular, the camera control unit 80 controls one of the methods illustrated on the basis of FIGS. 4, 5 and 6.

Figure 2:
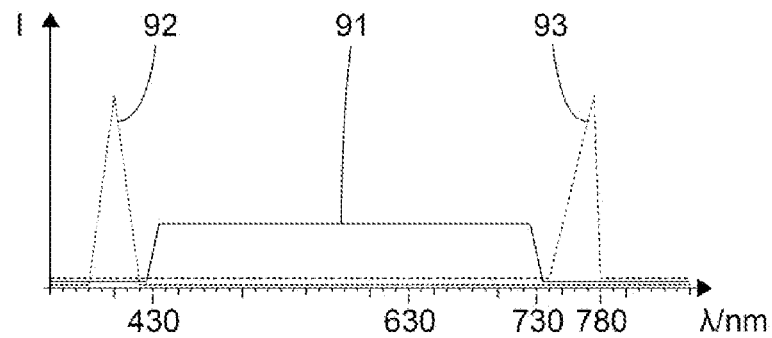
FIG. 2 shows a schematic illustration of spectra which are generated by a light-source device of the image capture system from FIG. 1.

FIG. 2 shows a schematic representation of the emission spectra of the light sources 21, 22, 23. The wavelength $\lambda$ in nm is assigned to the abscissa while the intensity I in arbitrary or relative units is assigned to the ordinate.

The spectrum 91 of the first light source 21 (cf. FIG. 1) or of the illumination light provided by the first light source 21, represented by a solid line, substantially comprises wavelengths between 430 nm and 730 nm and is substantially constant, i.e., wavelength independent, within these limits in the illustrated example.

The spectrum 92 of the second light source 22 or of the first excitation light provided by the second light source 22, represented by a line with short dashes, is narrowband. In the illustrated example, the spectrum 92 of the second light source 22 has a maximum at 400 nm to 410 nm and comprises only or substantially only wavelengths shorter than 430 nm.

The spectrum 93 of the third light source 23, i.e., of the second excitation light generated by the third light source 23, represented by a line with longer dashes, is narrowband. In the illustrated example, the spectrum 93 of the third light source has a maximum at approximately 770 nm to 780 nm and comprises only or substantially only wavelengths longer than 730 nm.

Figure 3:
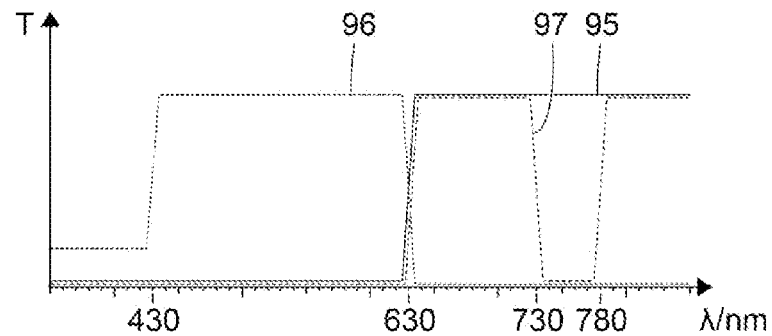
FIG. 3 shows a schematic illustration of spectral characteristics of a beam splitter and of filters of the image capture system from FIG. 1.

FIG. 3 shows a schematic representation of the transmission characteristics of the dichroic surface 51 of the beam splitter 50, and of the filters 56, 57 (cf. FIG. 1). The wavelength $\lambda$ in nm is assigned to the abscissa while the transmission T is assigned to the ordinate.

The transmission 95 of the dichroically reflecting surface 51 of the beam splitter 50, represented by a full line, is low at wavelengths shorter than a threshold wavelength $\lambda_0$ of approximately 630 nm, i.e., substantially 0, and high at wavelengths longer than the threshold wavelength $\lambda_0$ of 630 nm, that is substantially 1=100%. The reflection R, not illustrated, complements the transmission 95, i.e., it is approximately R=1-T.

The transmission 96 of the first filter 56, illustrated by a line with short dashes, is low, but not 0, at wavelengths shorter than 430 nm in order to allow some of the first excitation light, which was emitted by the second light source 22 and reemitted and/or reflected by the medical object 12, to reach the first image sensor 60. The transmission 96 of the first filter 56 is high, in particular approximately 1=100%, at wavelengths between 430 nm and 630 nm. In the illustrated example, the transmission 96 of the first filter 56 is small, in particular substantially 0, at wavelengths longer than 630 nm.

Deviating from the illustration in FIG. 3, the transmission 96 of the first filter 56 can be significant, in particular be substantially 1=100%, even at wavelengths greater than 630 nm. In this case and deviating from the illustration in FIG. 1, the first filter 56 can be arranged in front of the beam splitter 50, i.e., upstream of the beam splitter 50 in the light path.

The transmission 97 of the second filter 57 in front of the second image sensor 70, illustrated by a line with longer dashes, is low, in particular substantially 0, in a wavelength range between 730 nm and 780 nm in order to completely or substantially completely suppress second excitation light, which is generated by the third light source 23 and reemitted and/or reflected by the medical object 12. The transmission 97 of the second filter 57 is high, in particular substantially 1=100%, at wavelengths longer than 780 nm and between 630 nm and 730 nm. In the illustrated example, the transmission 97 of the second filter 57 is low, in particular substantially0, at wavelengths shorter than 630 nm.

Alternatively and deviating from the illustration in FIG. 3, the transmission 97 of the second filter 57 can be high even at wavelengths shorter than 630 nm. In this case, the second filter 57 can be arranged in front of the beam splitter 50.

Deviating from the illustration in FIG. 1, instead of having two filters 56, 57 after the beam splitter 50, i.e., downstream of the beam splitter 50 in the light path and hence between the beam splitter 50 and the image sensors 60, 70, both filters 56, 57 can be arranged in front of the beam splitter 50, i.e., upstream of the beam splitter 50 in the light path. Alternatively, provision can be made for a single filter in front of the beam splitter 50, i.e., upstream of the beam splitter 50 in the light path. In a manner similar to what is indicated in FIG. 3, this only filter substantially but not completely (or deviating from the illustration in FIG. 3: completely) suppressed first excitation light, which is generated by the second light source 22 and reemitted and/or reflected by the medical object 12, with wavelengths shorter than 430 nm, suppressed second excitation light (cf. spectrum 93 in FIG. 2), which is generated by the third light source 23 and reemitted and/or reflected by the medical object 12, in the wavelength range from 730 nm to 780 nm and completely or substantially completely transmitted both light between 430 nm and 730 nm and light with wavelengths longer than 780 nm.

Both the spectra 91, 92, 93 of the light sources 21, 22, 23 and the transmission spectra 95, 96, 97 can be slightly shifted in relation to the wavelengths illustrated on the basis of FIGS. 2 and 3. However, in this case the spectra 92, 93 of the second light source 22 and of the third light source 23 should be chosen such that the fluorescence of protoporphyrin IX and the fluorescence of OTL38 are excited as efficiently as possible and with the narrowest possible bandwidth. Further, the transmission spectrum 95 and the complementary reflection spectrum of the beam splitter 50 should be chosen such that as much as possible of the illumination light generated by the first light source 21 but as little as possible of the fluorescence light generated by protoporphyrin IX or OTL38, in particular no fluorescence light at all, is incident on the first image sensor 60. Further, the transmission spectra 96, 97 of the filters 56, 57 or of an alternative single filter in front of the beam splitter 50 should be chosen such that first excitation light, which is generated by the second light source 22 and reemitted and/or reflected by the medical object 12, falsifies the color impression in the color image captured by the first image sensor 60 as little as possible and second excitation light, which is generated by the third light source 23 and reemitted and/or reflected by the medical object 12, is incident to the smallest possible extent on the second image sensor 70.

As an alternative to the spectra illustrated on the basis of FIG. 2, the spectrum 91 of the illumination light provided by the first light source 21 can have a lower intensity or a much lower intensity or even a vanishing intensity at wavelengths longer than the threshold wavelength $\lambda_0$. In this case, the second image sensor 70 only receives correspondingly little or no reemitted and/or reflected illumination light, but predominantly or exclusively fluorescence light.

FIG. 4 shows a schematic flowchart of a method for capturing an image of a medical object 12 in reemitted and/or reflected illumination light, for capturing an image of the medical object 12 in fluorescence light generated by protoporphyrin IX and for capturing an image of the medical object in fluorescence light generated by OTL38. In particular, the method can be carried out using the image capture system 10 illustrated on the basis of FIGS. 1 to 3 and under control of the camera control unit 80 of the image capture system 10, but alternatively it can also be carried out by a system with features, properties and functions that deviate from the image capture system illustrated on the basis of FIGS. 1 to 3. Reference signs from FIGS. 1 to 3 are used in exemplary fashion.

In a method step 101, the medical object 12 is irradiated by illumination light with a broad spectrum 91, which comprises components in the wavelength ranges perceived as blue, green, and orange to red by the healthy human eye. In a further method step 102, which is carried out at the same time, the medical object 12 is irradiated by first excitation light for the purposes of exciting the fluorescence of protoporphyrin IX. In a further method step 103, which is carried out at the same time, the medical object 12 is irradiated by second excitation light for the purposes of exciting the fluorescence of OTL38. In a further method step 106, which is carried out at the same time, a first image sensor 60 is used to capture a color image in reemitted and/or reflected illumination light in the spectral ranges perceived as blue, green, and orange to red by the healthy human eye. In a further method step 107, which is carried out at the same time, a second image sensor 70 is used to capture an image of the medical object 12, which is referred to as fluorescence image, in fluorescence light generated by protoporphyrin IX and/or in fluorescence light generated by OTL38. The fluorescence of protoporphyrin IX and the fluorescence of OTL38 can be captured together in a monochrome fluorescence image or can be captured in two different color channels of a fluorescence image.

An image signal containing both information from the color image and information from the fluorescence image is generated in a further method step 111.

In a further method step 112, an image is displayed under control of the image signal generated in method step 111, said display being implemented, for example, by one or more monitors, a projector and/or virtual reality or augmented reality goggles.

Deviating from the illustration in FIG. 4, the broadband illumination light and the first excitation light and the second excitation light need not be generated at the same time and the color image and the fluorescence image need not be captured at the same time. Especially if the fluorescence image is captured by a monochrome image sensor 70 which has only one color channel in which both the fluorescence of protoporphyrin IX and the fluorescence of OTL38 are captured, only partial simultaneity may be advantageous in order to distinguish the fluorescence of protoporphyrin IX and the fluorescence of OTL38. An only partial simultaneity deviating from the illustration in FIG. 4 can further facilitate a correction of the image signal in the red color channel and hence a better color reproduction. Examples of such modified methods are shown in FIGS. 5 and 6.

FIG. 5 shows a schematic illustration of a flowchart of a further method for capturing an image of a medical object in reemitted and/or reflected broadband illumination light, for capturing an image of the medical object in fluorescence light generated by protoporphyrin IX and for capturing an image of the medical object 12 in fluorescence light generated by OTL38.

The method shown in FIG. 5 differs from the method illustrated on the basis of FIG. 4 in that, initially, only the irradiation 101 with illumination light, the irradiation 102 with first excitation light, the capture 106 of a color image and the capture 107 of a first fluorescence image (specifically in fluorescence light generated by protoporphyrin IX) occur simultaneously during a first time interval, but not the irradiation with the second excitation light. Only in a subsequent, non-overlapping second time interval are the irradiation 101 with broadband illumination light, the irradiation 103 with second excitation light, the capture 106 of a color image and a capture 108 of a second fluorescence image (specifically in fluorescence light generated by OTL38) implemented simultaneously, but not the irradiation with first excitation light. In this way, it is possible to distinguish between the fluorescence of protoporphyrin IX and the fluorescence of OTL38, and in the image signal generated in subsequent steps 111, 112 and in the displayed image controlled thereby it is possible to characterize or mark or emphasize the fluorescence of protoporphyrin IX and the fluorescence of OTL38 differently.

In an alternative deviating from FIG. 5, only steps 101, 102, 106, 107 and, subsequently, steps 111, 112 are carried out, as a result of which an image of the medical object 12 in reemitted and/or reflected illumination light and an image of the medical object 12 in fluorescence light generated by protoporphyrin IX are captured, but no image of the medical object 12 is captured in fluorescence light generated by OTL38. In a further alternative deviating from FIG. 5, only steps 101, 103, 106, 108 and, subsequently, steps 111, 112 are carried out, as a result of which an image of the medical object 12 in reemitted and/or reflected illumination light and an image of the medical object 12 in fluorescence light generated by OTL38 are captured, but no image of the medical object 12 is captured in fluorescence light generated by protoporphyrin IX.

FIG. 6 shows a schematic flowchart of a further method for capturing an image of a medical object in reemitted and/or reflected broadband illumination light, for capturing an image of the medical object in fluorescence light generated by protoporphyrin IX and for capturing an image of the medical object in fluorescence light generated by OTL38.

The method shown in FIG. 6 differs from the method illustrated on the basis of FIG. 5 in that, in particular, the medical object 12 is irradiated by red light, i.e. light in the wavelength range perceived as red by the healthy human eye and, at the same time, a red light image in reemitted and/or reflected red light is captured by means of the second image sensor in a third time interval, without the medical object 12 being irradiated by first excitation light or by second excitation light at the same time. As a result, only the red light reemitted and/or reflected by the medical object 12, and not fluorescence, is captured in a method step 109—by the second image sensor 70 in the image capture system illustrated on the basis of FIGS. 1 to 3. In a subsequent step 110, the red light image can be used to correct the red color channel of the color image and hence can be used to improve the color reproduction. Instead of an irradiation with red light, i.e., with light that only has spectral components in the wavelength range perceived as red by the healthy human eye, it is possible to use light containing further wavelength ranges, for example broadband illumination light as used in step 101. In this case, the medical object 12 can be irradiated continuously by the broadband illumination light with components in the wavelength ranges perceived as blue, green, and red by the healthy human eye.

In the method shown in FIG. 6, capture of a first fluorescence image and capture of a second fluorescence image are envisaged in two different and non-overlapping time intervals, similar to the method illustrated on the basis of FIG. 5. Alternatively, like in the method illustrated on the basis of FIG. 4, the fluorescence of protoporphyrin IX and the fluorescence of OTL38 can be captured simultaneously.

In each of the methods illustrated on the basis of FIGS. 4 to 6, the second image sensor 70 can receive and capture both reemitted and/or reflected illumination light and fluorescence light generated by protoporphyrin IX and/or by OTL38 within the wavelength range between the threshold wavelength $\lambda_0$ and approximately 730 nm in method steps 107, 108. If the medical object 12 is irradiated continuously by illumination light generated by the first light source 21, it is possible to obtain a pure fluorescence image as a difference between an image captured by the second image sensor during the illumination with both illumination light and excitation light, and an image captured during the illumination with illumination light only.

If the medical object 12 is not irradiated continuously by illumination light generated by the first light source 21, it is possible to capture a pure fluorescence image while the medical object 12 is only illuminated by excitation light.

As indicated above, the intensity of the illumination light generated by the first light source 21—deviating from the illustration in FIG. 2—can be small or even vanishing at wavelengths longer than the threshold wavelength $\lambda_0$. In this case, even if the first light source 21 generates illumination light continuously, the second image sensor 70 receives little or no illumination light, which is generated by the first light source 21 and reemitted and/or reflected by the medical object 12. Rather, most or all of the light received by the second image sensor 70 is fluorescence light and the image captured by the second image sensor 70 is a pure or almost pure fluorescence image.

If the illumination light generated by the first light source 21 only has a low intensity or vanishing intensity at wavelengths above the threshold wavelength $\lambda_0$, the methods described on the basis of FIGS. 4 to 6 can be particularly advantageous. A fourth light source for generating light in the wavelength range above the threshold wavelength $\lambda_0$ perceived as red by the healthy human eye is in particular further provided in this case in the method described on the basis of FIG. 6, in order to illuminate the medical object 12 in this wavelength range within the scope of method step 104.

Figure 7:
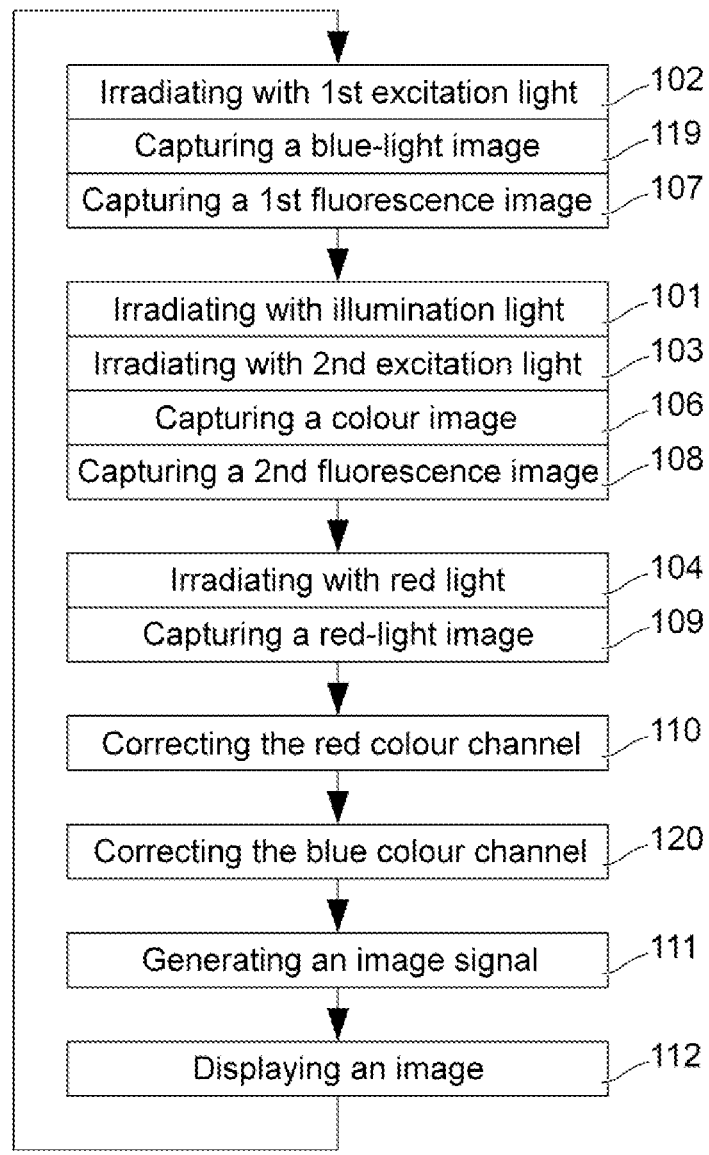
FIG. 7 shows a schematic flowchart of a further method for capturing images.

FIG. 7 shows a schematic flowchart of a further method for capturing an image of a medical object in reemitted or reflected broadband illumination light, for capturing an image of the medical object in fluorescence light generated by protoporphyrin IX and for capturing an image of the medical object in fluorescence light generated by OTL38.

The method shown in FIG. 7 differs from the method illustrated on the basis of FIG. 6 in terms of the first time interval, in particular. During the first time interval, the medical object 12 is irradiated 102 merely by first excitation light, but not by illumination light. During the first time interval, the second image sensor 70 simultaneously captures 107 a first fluorescence image in fluorescence light generated by protoporphyrin IX, like in the methods illustrated on the basis of FIGS. 4 to 6. In contrast to the methods illustrated on the basis of FIGS. 4 to 6, no color image is captured in the first time interval. However, a blue-light image in reemitted and/or reflected first excitation light is captured 119 by the blue color channel of the first image sensor 60 during the first time interval, simultaneously with the irradiation 102 with first excitation light.

In the second time interval, the method shown in FIG. 7 is similar to the methods shown in FIGS. 5 and 6.

In a later method step 120, the blue color channel of the color image captured during the second time interval is corrected, in particular by adding the blue-light image captured during the first time interval. This correction can add the diffuse and specular reflection properties of the medical object 12 to the color image at wavelengths shorter than 430 nm and hence improve the color reproduction.

The method described on the basis of FIG. 7 can be carried out both with a first light source 21 which only generates a low or vanishing intensity above the threshold wavelength $\lambda_0$ and with a first light source 21 which generates a substantial intensity above the threshold wavelength $\lambda_0$ (as shown in FIG. 2).

Figure 8:
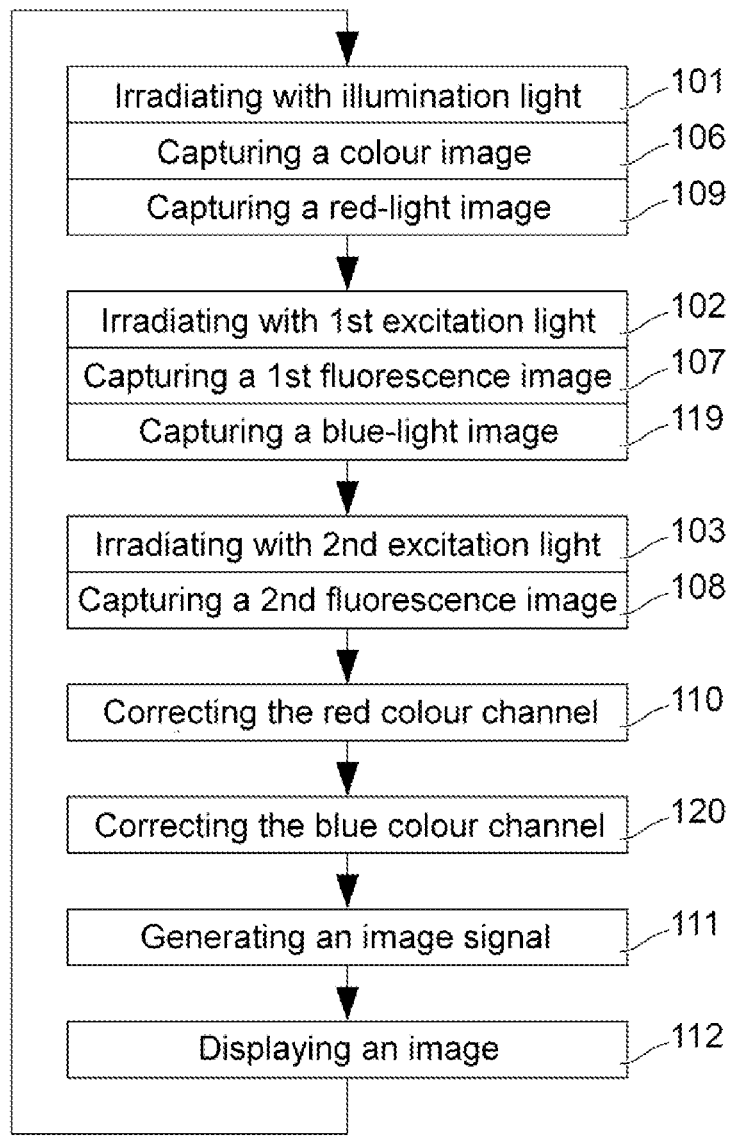
FIG. 8 shows a schematic flowchart of a further method for capturing images.

FIG. 8 shows a schematic flowchart of a further method for capturing an image of a medical object in reemitted and/or reflected broadband illumination light, for capturing an image of the medical object in fluorescence light generated by protoporphyrin IX and for capturing an image of the medical object in fluorescence light generated by OTL38.

The method shown in FIG. 8 differs from the methods illustrated on the basis of FIGS. 4 to 7 in that, in particular, the capture 106 of the color image, the capture 107 of the first fluorescence image and the capture 108 of the second fluorescence image is implemented in three different and non-overlapping time intervals.

In a first time interval, the medical object 12 is irradiated 101 by illumination light and a color image is captured at the same time by means of the first image sensor 60. If the illumination light in the wavelength range captured by the second image sensor 70 has a substantial intensity, a red light image can be captured simultaneously by means of the second image sensor 70 in an optional method step 109. This red light image can be used in a subsequent method step 110 for correcting the red color channel of the color image captured by means of the first image sensor 60.

In a second time interval, the medical object 12 is irradiated 102 by first excitation light and a first fluorescence image in fluorescence light generated by protoporphyrin IX is captured at the same time by means of the second image sensor 70. If the blue color channel of the first image sensor 60 receives first excitation light reemitted and/or reflected by the medical object 12, a blue-light image in reemitted and/or reflected first excitation light can be captured simultaneously by means of the first image sensor 60 in an optional method step 119. This blue-light image can be used in a subsequent method step 120 for correcting the blue color channel of the color image captured by means of the first image sensor 60.

In a third time interval, the medical object 12 is irradiated 103 by second excitation light and a second fluorescence image in fluorescence light generated by OTL38 is captured 108 at the same time by means of the second image sensor 70.

An image capture system 10 as described on the basis of FIGS. 1 to 3 can have a plurality of different modes of operation, in which the methods described on the basis of FIGS. 4 to 8, parts of these methods and/or further methods are carried out. In particular, each of the methods described on the basis of FIGS. 5 and 6 can be modified by virtue of dispensing with either the method steps 101, 102, 106, 107 carried out in the first time interval or the method steps 101, 103, 106, 108 carried out in the second time interval. Further, the image capture system 10 can have one or more modes of operation, within the scope of which only a white-light image is captured and/or only a white-light image without fluorescence information is displayed. Further, the image capture system 10 can have one or more modes of operation, within the scope of which only a fluorescence image is captured and/or only a fluorescence image without white-light image information is displayed.

Although the invention and its advantages have been described in detail, it should be understood that various changes, substitutions and alterations can be made herein without departing from the scope of the invention as defined by the appended claims. The combinations of features described herein should not be interpreted to be limiting, and the features herein may be used in any working combination or sub-combination according to the invention. This description should therefore be interpreted as providing written support, under U.S. patent law and any relevant foreign patent laws, for any working combination or some sub-combination of the features herein. Moreover, the scope of the present application is not intended to be limited to the particular embodiments of the process, machine, manufacture, composition of matter, means, methods and steps described in the specification. As one of ordinary skill in the art will readily appreciate from the disclosure of the invention, processes, machines, manufacture, compositions of matter, means, methods, or steps, presently existing or later to be developed that perform substantially the same function or achieve substantially the same result as the corresponding embodiments described herein may be utilized according to the invention. Accordingly, the appended claims are intended to include within their scope such processes, machines, manufacture, compositions of matter, means, methods, or steps.

The invention claimed is:

1. A method for capturing an image of a medical object in reemitted and/or reflected illumination light and for capturing an image of the medical object in fluorescence light generated by protoporphyrin and for capturing an image of the medical object in fluorescence light generated by OTL38, comprising the steps of:
irradiating the medical object with an illumination light in the blue, green and red spectral range;

irradiating the medical object with illumination light in the blue, green and red spectral range or irradiating with red light in the red spectral range;

irradiating the medical object with a first excitation light for exciting fluorescence of protoporphyrin;

irradiating the medical object with a second excitation light for exciting fluorescence of OTL38;

capturing a color image of the medical object in the blue, green and red spectral range by means of a first image sensor;

capturing a fluorescence image of the medical object in the red and infrared spectral range by means of a second image sensor;

capturing a red light image of the medical object in the red spectral range by means of the second image sensor while irradiating the medical object with illumination light in the blue, green and red spectral range or with red light in the red spectral range; and correcting the red color channel of the color image on the basis of the red light image, wherein reemitted and/or reflected second excitation light is not captured or only partly captured by the second image sensor; and wherein the medical object is not irradiated by the second excitation light while the red light image is being captured.

2. The method for capturing an image of a medical object of claim 1, wherein all the steps of irradiating with illumination light in the blue, green and red spectral range; the step of irradiating with the first excitation light; the step of irradiating with the second excitation light; the step of capturing the color image in the blue, green and red spectral range by means of the first image sensor; and the step of capturing the fluorescence image in the red and infrared spectral range by means of the second image sensor occur at the same time.

3. The method of claim 1, wherein the medical object is not irradiated by the first excitation light while the red light image is being captured.

* * * * *